(12) United States Patent
Kaiser et al.

(10) Patent No.: US 8,518,941 B2
(45) Date of Patent: Aug. 27, 2013

(54) EXTREME TEMPERATURE AQUEOUS DECONTAMINATION COMPOSITION

(75) Inventors: Herbert J. Kaiser, Pontoon Beach, IL (US); Daniel A. Klein, Shiloh, IL (US); Anchalee Thanavaro, Definance, MO (US); Miranda Chevon Shaver, Saint Louis, MO (US)

(73) Assignee: American Sterilizer Company, Mentor, OH (US)

( * ) Notice: Subject to any disclaimer, the term of this patent is extended or adjusted under 35 U.S.C. 154(b) by 331 days.

(21) Appl. No.: 12/806,731

(22) Filed: Aug. 19, 2010

(65) Prior Publication Data
US 2012/0108593 A1 May 3, 2012

(51) Int. Cl.
*A01N 43/66* (2006.01)
*A61K 31/53* (2006.01)

(52) U.S. Cl.
USPC ........................................... 514/241

(58) Field of Classification Search
None
See application file for complete search history.

(56) References Cited

U.S. PATENT DOCUMENTS

| 6,525,237 B1 | 2/2003 | Purdon et al. |
| 2007/0213248 A1 | 9/2007 | Ohba et al. |
| 2008/0267904 A1* | 10/2008 | Taylor et al. ............... 424/78.37 |
| 2008/0272051 A1 | 11/2008 | Baseeth et al. |
| 2008/0299168 A1 | 12/2008 | Dadey et al. |

* cited by examiner

*Primary Examiner* — James D Anderson
*Assistant Examiner* — William Lee
(74) *Attorney, Agent, or Firm* — Hudak, Shunk & Farine Co. LPA

(57) ABSTRACT

An extreme temperature decontamination composition such as a solution for destroying microorganisms, chemical warfare and bioterrorism agents is utilized that generally does not freeze at low temperatures down to about minus 25° F. and also has no significant evaporation or decomposition at temperatures up to about 120° F. The solution is effective against nerve agents and vesicants such as VX and HD, and various biological agents. The composition comprises a metallic salt of dichloroisocyanuric acid or dibromoisocyanuric acid, an aqueous solvent system comprising polar compounds such as water and an alkyl glycol, and a quasi hydrophilic compound. The composition can be formulated as a one part system wherein all components are blended together.

19 Claims, 7 Drawing Sheets

**Chemical Warfar Agents -
Decontamination with Solvent System + DCICA**

| Chemical Warfare Agent | % Decontamination |
|---|---|
| HD | 100.0 |
| VX | 100.0 |

FIG. 1

EXTREME TEMPERATURE AQUEOUS DECONTAMINATION COMPOSITION

This invention was made with government support issued by the US Army RDECOM ACQ CTR. The Government has certain rights in the invention

FIELD OF THE INVENTION

The invention relates to an aqueous decontamination composition that is effective against organisms including microorganisms, chemical warfare agents and bioterriorism agents over a surprisingly wide temperature range, is non-flammable, has low viscosity, and is environmentally friendly. The composition generally comprises a metal salt of a dichloroisocyanuric acid or a dibromoisocyanuric acid, an aqueous solvent system containing polar compounds such as water and a glycol, and a quasi hydrophilic compound. Microorganism reductions up to log 6 are readily obtained.

BACKGROUND OF THE INVENTION

Chemical and Biological Warfare Agents (CWA and BWA, respectively) remain a threat in present military endeavors. Nerve agents, vesicants and biological agents can be encountered in all parts of the world in widely diverse climatic conditions. To address this challenge, decontamination systems are required that work under extreme weather conditions. A single decontaminant that is efficacious at both ends of the temperature spectrum would reduce logistics by preventing the need for fielding multiple decontaminant formulations.

Currently, materials used in the decontamination of surfaces contaminated with chemical and biological warfare agents are predominantly aqueous based systems that display optimal activity near or above room temperature. At low temperatures (below the freezing point of water) these systems tend to freeze or their reactivity decreases to almost zero, or the contact times required are unreasonably long. Conversely, at high temperatures many decontaminants decompose rapidly due to their reactive natures and, as they are typically aqueous solutions, they evaporate rapidly from surfaces thereby limiting their exposure to the targeted agents.

In addition, there are many instances where a low temperature/sterilant is required in industry. Examples of this are low temperature clean rooms, low temperature manufacturing areas, meat lockers, etc.

U.S. Pat. No. 3,169,906 relates to a sterile topical aerosol preparation and the process for preparing the same. More particularly it relates to self-sterilizing human topical aerosol preparations comprising 20 to 500 p.p.m. of an alkylene oxide which compound is introduced into a pressurized aerosol dispenser in admixture with a propellant such that the concentration of said alkylene oxide to said propellant is in the range of 40 to 1000 p.p.m. and preferably 40 to 400 p.p.m.

U.S. Pat. Nos. 5,236,614, 6,123,950, and U.S. Publication 2006/0008494 generally relate to disinfecting and bleaching compositions that can contain silicone compounds, alcohol solvents, or detergents.

U.S. Pat. Nos. 6,706,677, 7,259,133, and 7,319,085 generally relate to compositions containing a lipophilic fluid and a bleach system for treating fabric articles such as clothing, linens and drapery.

U.S. Publication 2004/0022672 relates to a method for disinfecting and/or sterilizing the hydraulic circuit within a dental unit by using active solutions.

U.S. Publication 2007/0244010 relates to providing a dichloroisocyanurate composition having storage stability, allegedly having low corrosiveness for various metals when used in an aqueous solution, and generating low irritating odor even when the concentration thereof in an aqueous solution is increased. The composition comprises a dichloroisocyanurate and sodium metasilicate pentahydrate in which only the particle surface is subjected to a treatment for reducing the degree of hydration.

GB 2 426 708 A relates to a multi-part disinfectant composition comprising parts which are packed separately prior to use, said parts when combined in water or an aqueous solution react to form chlorine dioxide. Preferably the separate parts are a metal chlorite e.g. sodium chlorite, and a mono-, di- or tri-chloroisocyanurate.

WO Publication 2006/085975 relates to organic decontamination compositions and methods of use thereof which include a biocide fraction dispersed in a substantially non-aqueous carrier and having less than about 10% by weight water. The biocide fraction contains biocidally effective organic peroxides, oxides, aldehydes, phenols, napthas and acids, quaternary ammonium compounds, transition metal salts, halogens, compounds containing a halogen, N, S or B atom, ozone and mixtures thereof.

WO Publication 2007/022610 relates to a method for treating coffee fruits with or without the pulp, comprising the step of contacting the coffee fruits with a solution of a composition selected from the group consisting of active chorine-releasing inorganic and organic compositions, such as calcium oxychloride, dichloroisocyanuric acid and sodium and potassium salts thereof and trichloroisocyanuric acid diluted in a liquid vehicle.

CN 101036622 relates to a disinfecting and sterilizing washing liquid for human body mainly with sodium dichloroisocyanurate is formed by combining solvent, sodium dichloroisocyanurate raw powder, pigment, spice and glycerin into raw liquid, which is capable of mixing with water in any proportion, and all medicines are maintained in the solvent.

CN 1615699 relates to an aerosol sterilizing agent consisting of sodium dichloroisocyanurate 100 weight portions, adipic acid 6-14 weight portions, potassium hypermanganate 8-12 weight portions and phenolic molding powder 4-8 weight portions. The bagged aerosol sterilizing agent is ignited to produce sterilizing and bleaching chlorine aerosol with good killing effect on *neurospora*, green mold, blue mold, *Aspergillus flavus, mucor*, etc. harmful to edible fungi.

CN 1631154 relates to a chlorine-containing effervescent disinfectant with low chlorine flavor, which can be chlorine-containing effervescent disinfection tablet, granule or powder. It is complexed from organic chlorine, surface activator and sodium salt, it can be dissolved rapidly in water and prepared into chlorine-containing disinfection liquid.

CN 1220089 relates to a disinfectant with quick killing action for gram-positive coccus, gram-negative *bacillus*, spore, fungi and various microorganisms of hepatitis virus and influenza virus, etc. Said fast composite disinfectant is made up by using active chlorine as effective main component for killing bacteria, and adding detersive disinfectant and protein denaturation disinfectant.

CN 1281824 relates to a sterilizing method for circulating water system that is characterized by adding inorganic alkaline compound in the circulating water containing germicide to make pH value be 9-12. Said invented sterilizing method can be used for inhibiting growth of microbe.

CN 101103728 relates to an agricultural sterilization combination comprising sodium dichloroisocyanurate, potassium dichloroisocyanurate and other active components.

JP 11-158008 relates to a composition that is obtained by coating (A) the surface of a solid compound releasing an active halogen of a chlorinated isocyanuric acid-based compound, 1,3-halogen-substituted-5,5-dimethylhydantoin, etc., with (B) a compound selected from (i) a higher alcohol sulfate salt and (ii) a higher saturated fatty acid (salt) and used in an amount of 0.5-50 wt. %, preferably 2-25 wt. % based on the component A.

SUMMARY OF THE INVENTION

A broad spectrum aqueous decontamination solution composition is disclosed that is effective over a broad temperature range, e.g. from about −25° F. (−32° C.) to about 120° F. (49° C.) without freezing or substantial evaporation, and comprises dichloro or dibromoisocyanuric acid or alkali metal salts thereof and various aqueous solvents such as water, ethylene or propylene glycol, alkyl lactate, and optionally alcohol or organic carbonates. The solutions generally have a pH as from about 4 to about 10, are nonflammable, stable, environmentally friendly, i.e. green solutions, and have suitable viscosities over the broad temperature range. The decontamination solution composition is very effective against microorganisms, chemical warfare and bioterrorism agents and yield log reductions of at least about 5, or about 6, or about 7 with respect to the same. Examples of various classes of compounds that can be decontaminated include spores, fungi, mycobacteria, vegetative bacteria, protozoa as well as other etiological agents including bioterrorism agents such as anthrax, botulisum, *brucella*, cholera, typhus fever, typhoid fever, and the like.

In one aspect of the invention, an extreme temperature aqueous decontamination solution comprises a metal salt of dichloroisocyanuric acid or of a dibromoisocyanuric acid; an aqueous solvent system comprising polar compounds including water and one or more alkyl glycols having from 2 to about 4 carbon atoms; and one or more quasi hydrophilic compounds comprising an alkyl lactate having from 1 to about 10 carbon atoms; wherein the amount of said polar compounds is from about 35% to about 90% by weight based upon the total weight of said polar compounds and said quasi hydrophilic compounds; wherein the amount of said metal salt of dichloroisocyanuric acid or said dibromoisocyanuric acid is from about 1 part to about 10 parts by weight per 100 parts by weight of said polar compounds and said quasi hydrophilic compounds; wherein said extreme temperature decontamination composition is essentially free of any organosilicon containing compounds, and wherein said extreme temperature decontamination composition is essentially free of any bleach.

A further aspect of the invention is a plurality of packages for forming an extreme temperature aqueous decontamination solution comprising a first package comprising a metal salt of dichloroisocyanuric acid or of a dibromoisocyanuric acid; and a second package comprising a solvent system comprising polar compounds including water and one or more alkyl glycols having from 2 to about 4 carbon atoms; and one or more quasi hydrophilic compounds comprising an alkyl lactate having from 1 to about 10 carbon atoms; wherein the amount of said polar compounds is from about 35% to about 90% by weight based upon the total weight of said polar compounds and said quasi hydrophilic compounds; wherein the amount of said metal salt of dichloroisocyanuric acid or said dibromoisocyanuric acid in said first package is from about 1 part to about 10 parts by weight per 100 parts by weight of said polar compounds and said quasi hydrophilic compounds; wherein said first package and said second package are essentially free of any organo silicon containing compounds, and wherein said first package and said second package are essentially free of any bleach.

Yet another aspect of the invention is a process for forming an extreme temperature aqueous decontamination solution comprising the steps of providing a metal salt of dichloroisocyanuric acid or of a dibromoisocyanuric acid; providing an aqueous solvent system comprising polar compounds including water and one or more alkyl glycols having from 2 to 4 carbon atoms; providing one or more quasi hydrophilic compounds comprising an alkyl lactate having from 1 to about 10 carbon atoms; wherein the amount of said polar compounds is from about 35% to about 90% by weight based upon the total weight of said polar compounds and said quasi hydrophilic compounds; wherein the amount of said metal salt of dichloroisocyanuric acid or dibromoisocyanuric acid is from about 1 part to about 10 parts by weight per 100 parts by weight of said polar compounds and said quasi hydrophilic compounds; and mixing said metal salt of dichloroisocyanuric acid or of dibromoisocyanuric acid, said polar compounds, and said quasi hydrophilic compounds and forming an aqueous decontamination solution.

BRIEF DESCRIPTION OF THE DRAWINGS

FIG. 1 relates to the efficacy of dichloroisocyanuric acid (DCICA) in a solvent system against the chemical agents HD and VX;

DETAILED DESCRIPTION OF THE INVENTION

Figure 2:
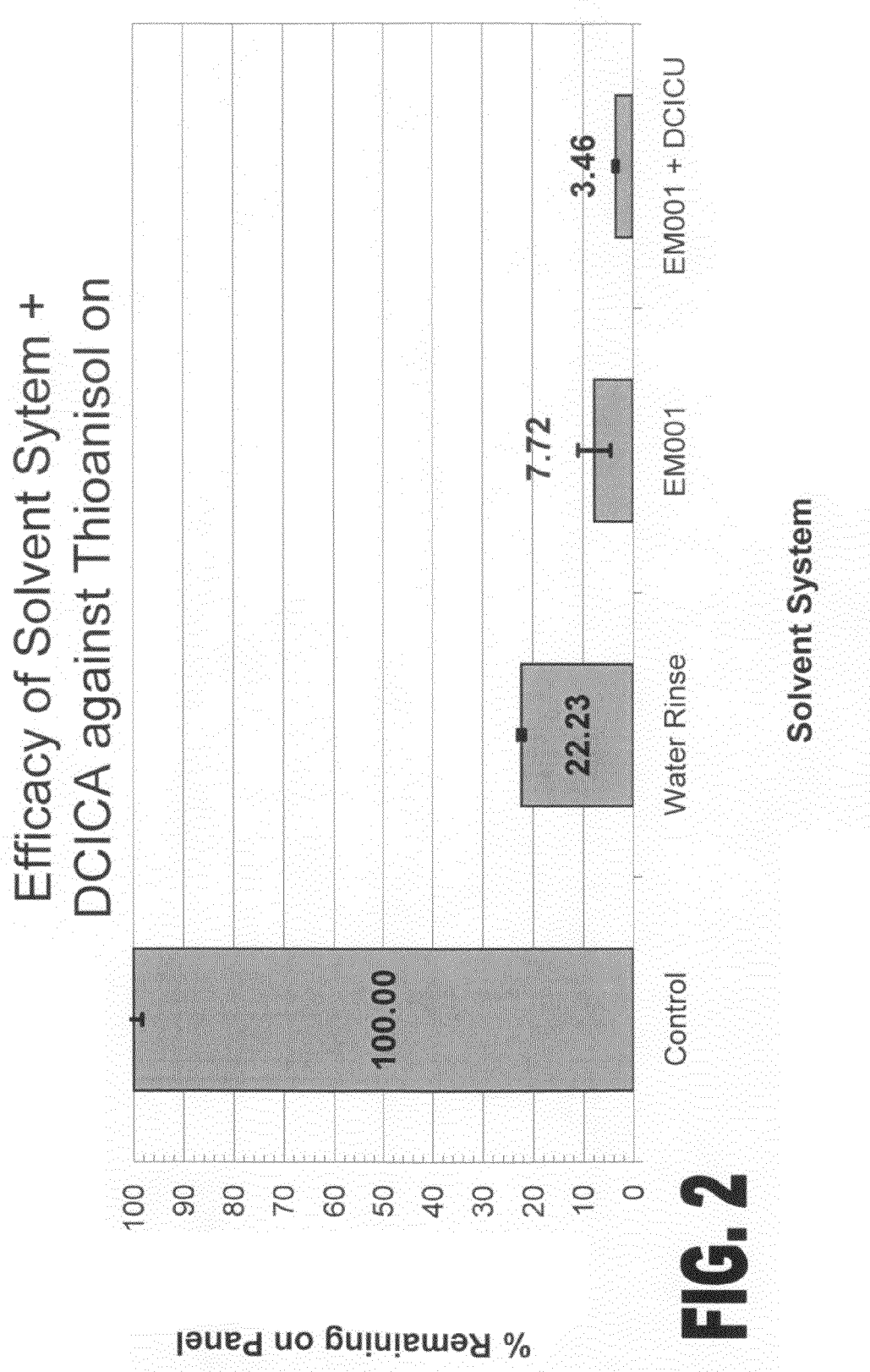
FIG. 2 relates to the efficacy of DCICA against thioanisole simulant on CARC panels.

The broad spectrum aqueous decontamination solution of the present invention is very effective in eradicating, destroying, or killing various types of microorganisms including, but not limited to various spores; various fungi; various mycobacteria; various vegetative bacteria; various protozoa; as well as various chemical warfare agents; and various bioterrorism agents. Examples of spores include endospores such as *Geobacillus stearothermophilus, Bacillus subtilis, Bacillus subtilis globigii, Clostridium sporogenes, Bacillus cereus*, and *Bacillus circulans*. Examples of fungi include *Aspergillus niger, Candida albicans, Trichophyton mentagrophytes*, and *Wangiella dermatitis*. Examples of mycobacteria include *Mycobacterium chelonae, Mycobacterium gordonae, Mycobacterium smegmantis*, and *Mycobacterium terrae*. Examples of vegetative bacteria include *Aeromonas hydrophila, Enterococcus faecalis, Streptococcus faecalis, Enterococcus faecium, Streptococcus pyrogenes, Escherichia coli, Klebsiella (pneumoniae), Legionella pneumophila, Methylobacterium, Pseudomonas aeruginosa, Samonella choleraesuis, Helicobacter pylori, Staphylococcus aureus, Staphylo-

*coccus epidermidis*, and *Stenotrophomonas maltophilia*. Examples of protozoa include *Giardia lamblia* and *Cryptospodidim parvum*.

Examples of chemical warfare agents that can be eradicated, or destroyed by the decontamination solutions of the present invention include: vesicants such as HD, and nerve agents including VX and any other phosphono-containing compounds.

Examples of bioterriorism agents that can be treated by the decontamination solutions of the present invention include anthrax (*Bacillus anthracis*), botulisum (*Clostridium botulinum* toxin), *brucella* species (brucellosis), *Burkholderia mallei* (glanders), *Burkholderia pseudomallei* (Melloidsis), *Chlamydia Psittaci* (psittacosis), cholera (*Vibrio cholerae*), *Clostridium perfringens* (Epsilon toxin), *Coxiella bumetii* (Q fever), emerging infectious diseases such as nipah virus and hantavirus, *Escherichia coli* 0157:H7 (*E. Coli*), food safety threats (e.g. *salmonella* species), *Francisella tularensis* (tularemia), plague (*Yersinia pestis*), ricin toxin from *Ricinus communis* (castor beans), *Rickettsia prowazekii* (typhus fever), *Salmonella typhi* (typhoid fever), *shigella* (shigellosis), smallpox (*Variola major*) Staphylococcal enterotoxin B, *Vibrio cholerae* (cholera), Viral encephalitis (alphaviruses [e.g. Venezuelan equine encephalitis, eastern equine encephalitis, western equine encephalitis], viral hemorrhagic fevers (filoviruses [e.g. Ebola, Marburg] and arenaviruses [e.g. Lassa, Machupol], water safety threats (e.g. *Cryptosporidium parvum*), and *Yersinia pestis* (plague), or any combination thereof.

As previously noted, the decontamination solutions have many advantages with respect to properties and applications thereof such as good stability at temperature extremes, low freezing points, low vapor pressure, non-flammability, low viscosity, compound compatibility, and environmental friendliness.

The aqueous contamination compositions of the present invention do not freeze at temperatures above about 0° F. (−18° C.) and preferably at temperatures above about −25° F. (−32° C.). Thus, good stability properties of the liquid decontamination compositions of the present invention generally exist at extreme temperatures of from about −25° F. (−32° C.) to about 120° F. (49° C.), desirably from about 0° F. (−18° C.) to about 110° F. (to about 43° C.) and preferably from about 10° F. (−12° C.) to about 100° F. (39° C.). With respect to general chemical properties, the decontamination solutions of the present invention are generally not harmful to the skin of humans and the vapors thereof are not harmful to the lungs.

Another important property of decontamination solutions of the present invention is that they are not flammable, have boiling points above 100° C. and have low vapor pressures. The evaporation rates of the decontaminant solutions are minimal. After 200 minutes, weight loss was <20% at 10° C., <50% at <20° C., and <90% at 50° C. for one embodiment. This evaporation rate is slow compared to the decontamination reaction time.

In addition to not freezing, the invention maintains a consistency suitable for pumping or pouring. The viscosity of the decontamination solutions generally ranges from about 120 centipoise or less, and desirably about 100 centipoise or less at temperatures of about −25° F. (−32° C.); generally about 50 or less, or about 40 or less, and even about 35 centipoise or less at temperatures of about 0° F. (−18° C.); and preferably about 20 centipoise or less at temperatures of about 10° F. (−12° C.). The lower limit of the viscosity at higher temperatures up to about 120° F. (49° C.) are generally less than about 20, desirably less than about 10, and preferably even less than about 5 centipoise.

Another important advantage of the decontamination solutions of the present invention is that the various components thereof are compatible with one another at the above-noted broad temperature ranges. The decontamination compositions also have good pot life generally of at least 4 hours and desirably at least 8 hours at 80° F. (27° C.). That is, they still are effective with regard to decontaminating various microorganisms, etc., after the noted pot life.

The decontamination solutions are also environmentally friendly in that they meet the EPA's definition of green chemistry. "Green chemistry is the design of chemical products and processes that reduce or eliminate the use or generation of hazardous substances." The breakdown products from this invention include ethanol, glycerin and other naturally occurring solvents as well as organic acids like lactic acid.

The decontamination compositions of the present invention can generally comprise either a one package system wherein all components have been blended together, or a two package system. With respect to the one-package composition, one component is an aqueous solvent system that comprises polar compounds as well as one or more quasi hydrophilic compounds. The polar composition includes water, generally in significant amounts as from about 20 to about 80%, desirably from about 30 to about 70%, and preferably from about 40 to about 60% by weight based upon the total weight of polar solvents. Other polar components that have been found very effective in achieving the above-noted various attributes of the present invention are various alkyl glycols having from 2 to about 4 carbon atoms, such as ethylene glycol with propylene glycol being preferred. The amount of such one or more glycols is generally from about 20 to about 80%, desirably from about 30 to about 70%, and preferably from about 40 to about 60% by weight based upon the total weight of the polar solvents.

The quasi hydrophilic compound includes one or more alkyl lactates wherein the alkyl group has from 1 to about 10 and desirably from 1 to about 3 carbon atoms, such as methyl lactate, ethyl lactate, or propyl lactate, with ethyl lactate being preferred. The amount of one or more lactates is generally from about 10 to about 65%, desirably from about 20 to about 50 or about 60%, and preferably from about 30% to about 40% or about 45% by weight with the remaining percent being the total weight of the polar compounds, that is the water and the one or more alkyl glycols. Thus, the total weight of the two or more polar compounds ranges from about 35% to about 90%, desirably from about 40% or about 50% to about 80%, and preferably from about 55% or about 60% to about 70% by weight based upon the total weight of the polar compounds and the quasi-hydrophilic compounds.

Another aspect of the present invention is the optional utilization of small amounts of an alkyl carbonate wherein the alkyl group contains from 2 to about 4 carbon atoms with propylene carbonate being preferred. Use of alkyl carbonates has been found to improve the solvent like characteristics of the invention. The amount of the one or more carbonates is generally from about 2 to about 20 parts, desirably from 4 to about 17 parts, and preferably from about 9 to about 13 parts by weight for every 100 parts by weight of the one or more polar compounds and the one or more quasi hydrophilic compounds.

The present invention, as noted above, relates to an aqueous decontamination solution and thus contains large amounts of polar compounds or solvents including water. Thus, compositions containing low amounts of polar compounds such as water, alcohols, glycols, glycol ethers, ethers, and the like are excluded from the present invention. By the term "low amounts" is generally meant amounts of polar compounds that are generally less than about 30% and preferably less than about 25% by weight based upon the total weight of the aqueous decontamination solution.

The decontaminant is dichloroisocyanuric acid (DCICA) or dibromoisocyanuric acid (DBICA) and/or desirably a metal salt, preferably an alkali metal salt, thereof such as lithium, sodium, or potassium with sodium being especially preferred. The amount of the decontamination compound, i.e., the one or more salts of dichloroisocyanuric acid or of dibromoisocyanuric acid, or both, is generally from about 0.1 to about 10, desirably from about 2 to about 9, and preferably from about 3.5 to about 8 parts by weight, per 100 parts by weight of the total weight of the one or more polar compounds and the one or more quasi-hydrophilic compounds.

The extreme temperature aqueous decontamination solution composition of the present invention can generally be prepared as a one part or a two part system, i.e. as a one package or a two package embodiment. With respect to the one package embodiment, the various components such as the polar compounds, the quasi hydrophilic compound, and the metal salt of dichloroisocyanuric acid or of dibromoisocyanuric acid can be mixed in generally any manner and then packaged. Upon utilization, the one package composition can be applied to any contaminated item such as a surface, substrate, article, apparatus, clothing, fabric, or a person, in any conventional manner, such as by spraying, roller application, brushing, dipping or immersing the article into the decontamination solution composition, and the like. If desired or required, a second application can subsequently be made.

In the preferred two part or two package embodiment of the present invention, the various liquid or soluble components are obtained or provided and mixed or blended together to form an aqueous or solvent mixture which is then contained in one package. Of course, the amount of the various liquid or solvent components is as set forth hereinabove. The second package relates to obtaining or providing a decontaminant and packaging the same. Both packages are then stored until required for use. Before application of the extreme temperature aqueous decontamination solution composition, both packages are mixed or blended, that is added to one another, and then applied in any conventional manner as noted hereinabove to a desired item, for example a substrate, article, etc. Once again, if so desired or required, one or more subsequent applications can be made.

It is also an aspect of the present invention that the water component of the liquid containing package can be either separately packaged or utilized at the source of application. However, this method is generally not desired inasmuch as an appropriate amount of water must be measured and also requires an additional mixing step.

The invention will be better understood by reference to the following examples which serve to illustrate, but not to limit the present invention.

Chemical agent simulants were selected for their ability to mimic specific behaviors or physical properties of the live agents HD and VX. The following simulants were selected:

HD decontamination simulants: 2-Chloroethyl Phenyl Sulfide (CEPS)

HD physical solubility: Thioanisole

VX decontamination simulant: Diethylmethylphosphonothioate (DEMPT)

Live agent results were compared to simulant data to confirm the correlation between the two.

High throughput screening using simulants was performed using a custom-developed reactor block apparatus'. The device has interchangeable temperature-controlled blocks that hold up to 24 reactor or gas chromatography vials. Using a standard reactor procedure, the simulant and compositions of the present invention were blended, the reaction was quenched and the mixture was tested using gas chromatography/mass spectrometry (GC-MS) to determine the amount of unreacted simulant remaining and/or the simulant reaction products. The chemical decontamination samples were primarily run on a GC-MS along with the appropriate controls and standards to permit quantitation of unreacted starting material and breakdown products.

[1](Tienes, B. M.; Thanavaro, A.; Kaiser, H. J. *Screening Methodologies for Chemical Warfare Agent Decontaminants* 2006 Denver Decon Science & Technology Conference, Oct. 31-Nov. 2, 2006, Westminster, Colo. (Poster)).

More specifically, the simulant was added to a vial followed by a solution of the active ingredient. The vial was then placed on the reactor block under controlled temperature and continuous agitation. The reaction was quenched with an appropriate solution and briefly vortex mixed. Chloroform was then added to extract the resulting mixture and the vial was again vortexed. The chloroform layer was analyzed using GC/MS to determine the amount of unreacted stimulant remaining and/or the simulant byproducts.

Temperature control for the reactor block apparatus was provided by a high capacity re-circulating bath capable of maintaining fixed reaction temperatures over the range of −32° C. to 50° C. The re-circulator in line with the reactor block maintained uniform mixing dynamics across all experiments. A control sample of the solvent mixture was placed in a vial and monitored to insure proper temperature maintenance during the reaction process.

Microbiological challenge tests were performed using *B. subtilis* spores as a surrogate for anthrax. Time kill studies were performed to evaluate the microbiological efficacy of the most promising decontamination formulae.

Chemical and microbiological decontamination rates were monitored over the entire range of temperature extremes from −25° F./−32° C. to 120° F./49° C.

The testing of various decontaminants revealed that dichloroisocyanuric acid (DCICA), was least impacted by temperature. Even at −30° C., DCICA achieved 100% decontamination of DEMPT (a VX simulant) within 5 minutes. (See FIG. 3) The DCICA was readily soluble with the polar solvents of the invention that provide usability at the noted extreme temperatures. In addition, it is non-flammable, generally stable and environmentally friendly, as well as being commonly available at a low cost.

Chemical and Biological Efficacy

Live Chemical Agent Efficacy

The use of simulants to perform initial screening studies provides a safer, more cost effective method for exploring the experimental space of a project. However, the behavioral characteristics of the decontaminant against the simulants are not always predictive of performance against live agents. Therefore, live agent testing was required to validate the use of simulants and to verify the behavior of the active in the solvent systems. NMR testing was completed at room temperature for ease of agent handling. Temperature control over the extremes of this temperature range was not feasible with live agents and this testing type. However, the room temperature testing had good correction to simulant testing which was used to correlate the HD and VX reactions at the temperature extremes.

The formulations utilized were as follows:

| Formulations (percent wt) | EM1001 | EM1002 |
|---|---|---|
| Ethyl lactate | 35% | 30% |
| Water | 34% | 29% |
| Propylene glycol | 31% | 31% |
| Sodium dichloroisocyanurate | 6% | 6% |
| Propylene carbonate | — | 10% |

Weight percent is based upon the total weight of the ethyl lactate, water, propylene glycol, and propylene carbonate. The amount of the DCICA is based upon the preceding components.

All solvent components were dispensed by volume. 3.5 mL of deionized water was combined with 3.0 mL of propylene glycol and 3.5 mL of ethyl lactate giving a final solvent volume of 10 mL. Dichloroisocyanuric acid sodium salt was used as the active. 0.6 grams of the active were added to the 10 mL of the solvent system and mixed until completely combined. Alternately—An aqueous solution of the present invention, Formulation EM1001 comprising 35% by weight of ethyl lactate, 31% by weight of propylene glycol, and 34% by weight of water utilizing 6 parts by weight of sodium dichloroisocyanurate per 100 parts by weight of the solution was prepared. Formulation EM1002 comprised 30% by weight of ethyl lactate, 31% by weight of propylene glycol, and 29% by weight of water along with 10% by weight of propylene carbonate utilizing 6 parts by weight of sodium dichloroisocyanuric acid per 100 total parts by weight of the other components. NMR testing was performed by combining 10 μL of VX or HD ($^{13}$C labeled) with 500 μL of the invention (above solution of solvents and active) in an NMR tube. Five inversions of the tube occurred to mix the sample (EM1001) and the agent. Samples were measured at the given time using a 600 MHz instrument. The agents and the reaction byproducts were monitored by $^{31}$P for VX and $^{13}$C for HD. The results are set forth in FIG. 1 wherein DCICA completely decontaminated HD and VX agents at 25° C.

The Effect of CARC Substrate on Efficacy

To address concerns that efficacy against the aqueous decontamination solution might be reduced on a CARC (chemical agent resistant coating) surface, an efficacy study was performed against Thioanisole, a HD-agent stimulant. Results utilizing EM1001 indicated successful decontamination after a five minute exposure to the decontaminant (FIG. 2). Visual observation of the panels after treatment did not reveal any apparent negative impact on the CARC surface.

Figure 3:
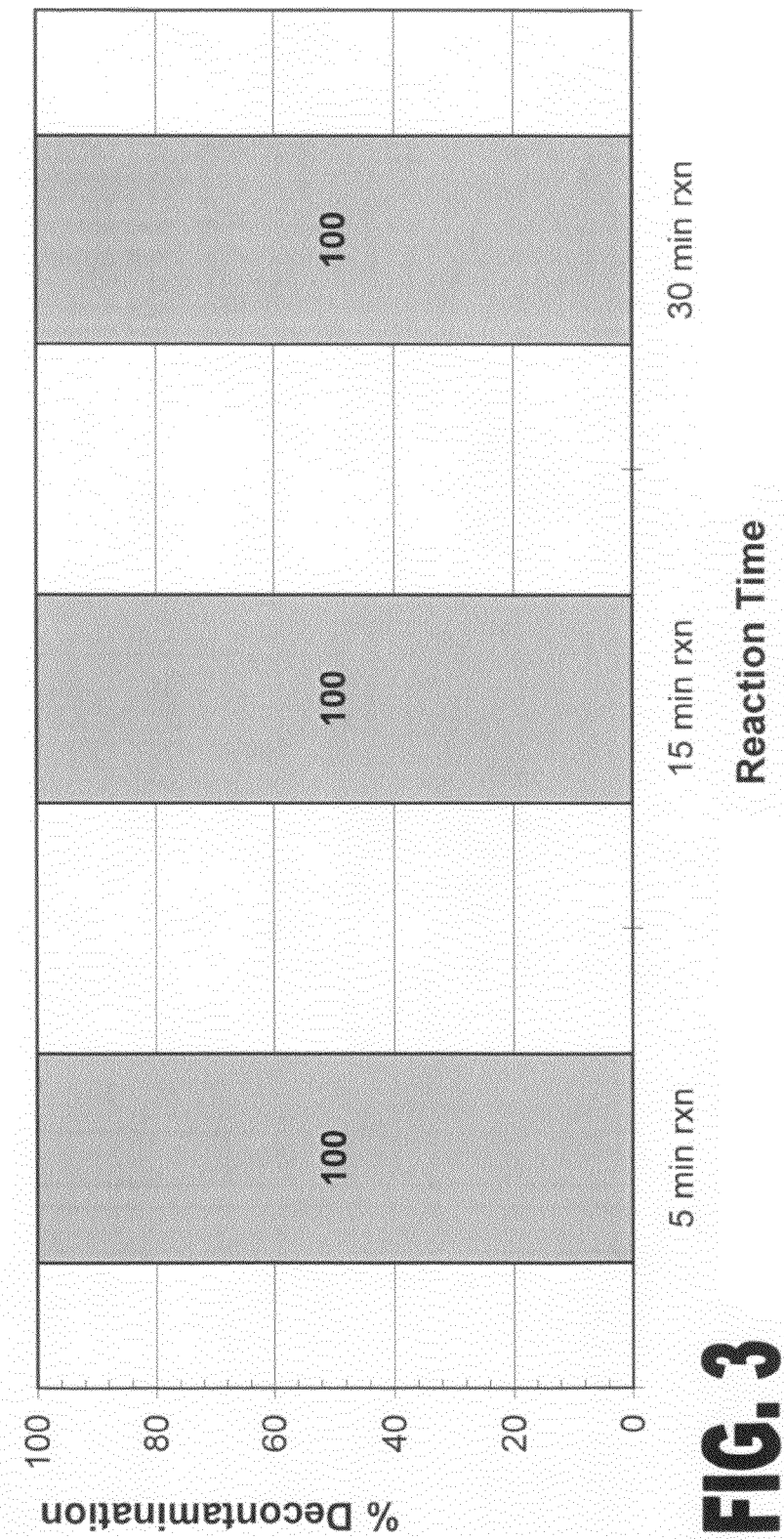
FIG. 3 relates to DCICA reaction time against DEMPT at −30° C.

In order to predict the temperature effect on chemical warfare agents at low temperatures, i.e. −30° C., EM1001 was tested against DEMPT (a VX simulant). (FIG. 3). Complete decontamination was obtained at times of 30, 15, and 5 minutes. This verified that chemical warfare agents can be decontaminated at sub-freezing temperatures.

Figure 4:
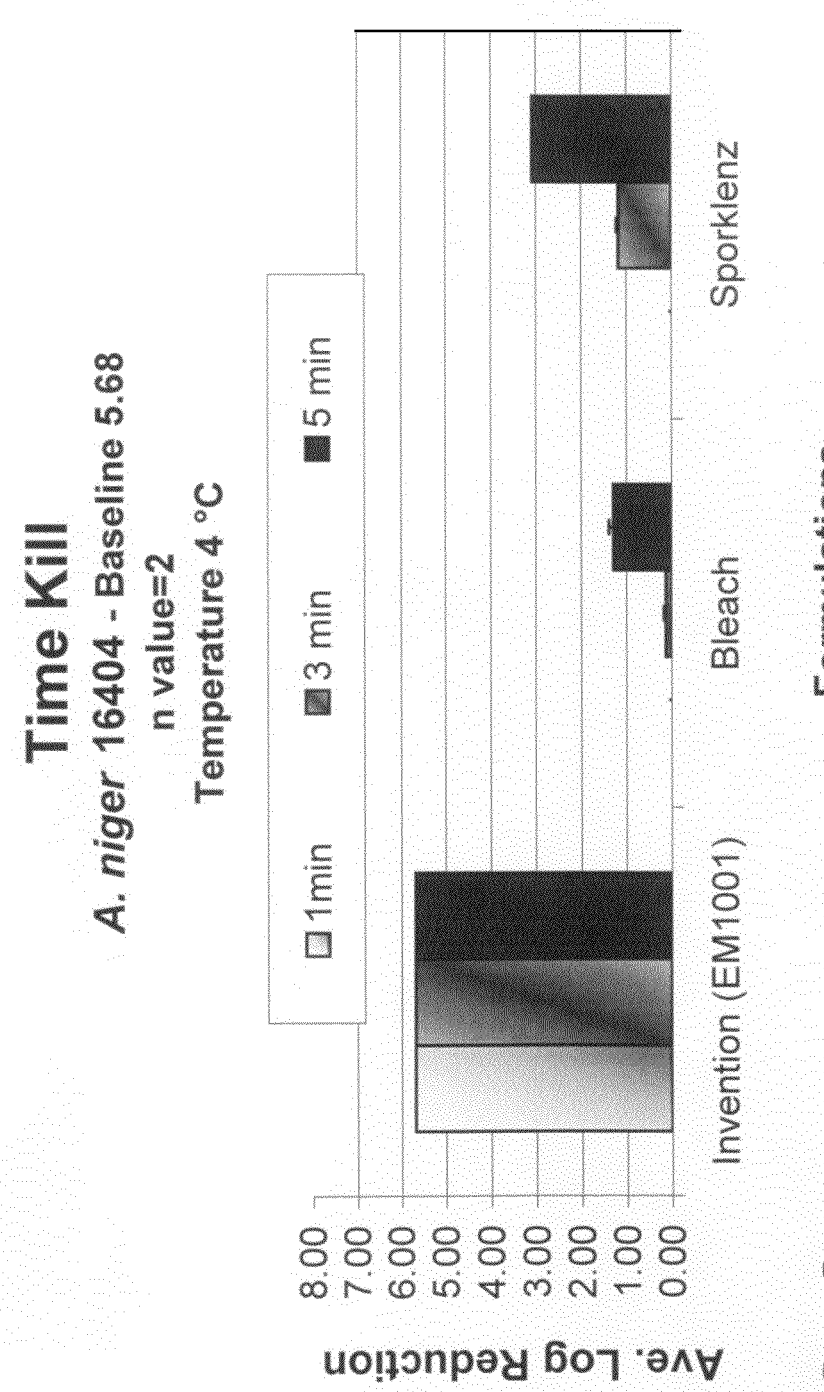
FIG. 4 relates to the biological efficacy of DCICA in a solvent system compared to bleach and SporKlenz RTU.

Another time kill study was completed to evaluate cold weather efficacy of the EM1001 formulation against non-spore organisms and to benchmark the efficacy against more commonly known materials. Disinfection of the mold *A. niger* (baseline 5.68) was tested at −3° C. against bleach and SporKlenz RTU (SK RTU), a peracetic acid-based sporicide. The results as set forth in FIG. 4 indicate that the proposed extreme weather formulation is significantly more effective against this organism than either bleach or SK RTU. Given the micro testing results of 6 log reduction at room temperature in five minutes, the higher temperatures were not tested. The chemistry reaction rates are very high already which would only increase the reaction time to less than five minutes. Additionally, the high end of the temperature extreme would provide an uninhabitable environment for the microbes tested, without the chemistry.

As apparent from the above examples, the microorganism, chemical warfare and bioterrorism agent decontamination solutions of the present invention had significant decontamination or eradication of microorganisms over a temperature range of from about −30° F. (−34° C.) or about −25° F. (−32° C.) to about 120° F. (49° C.). The aqueous solvent system of the present invention was demonstrated to provide favorable advantages and properties such as low viscosity, low freezing points, nonflammability, environmental friendliness, and the like.

Effect of Increasing pH on *B. Subtilis*

Figure 5:
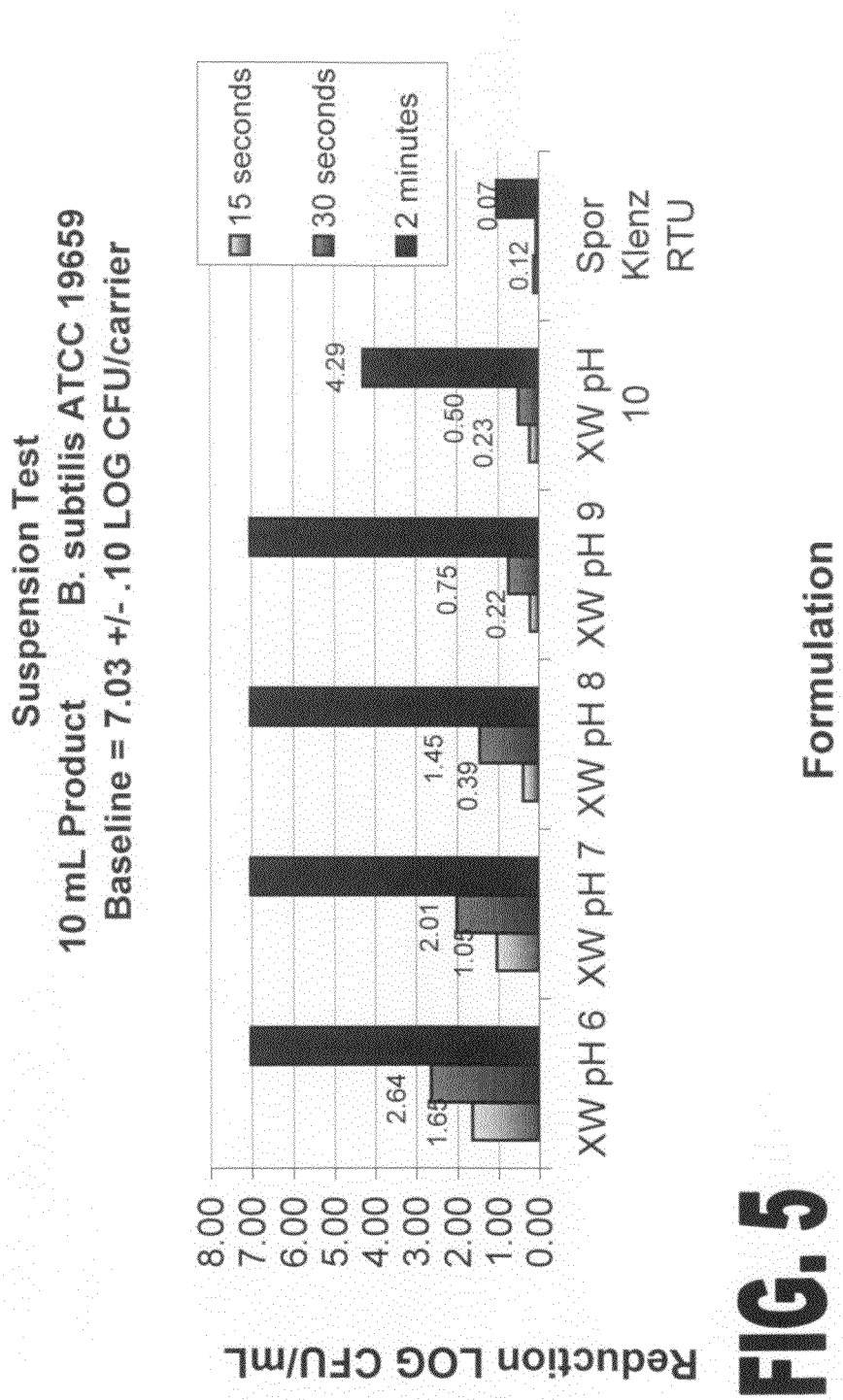
FIG. 5 relates to the efficacy of DCICA against *B. Subtilis* at various pH.

As apparent from FIG. 5, the decontamination aqueous solution EM1001 of the present invention resulted in a 7 log reduction from about pH 4 to about pH 10. In comparison, a commercial product, i.e. SporKlenz RTU, a peracetic acid-based sporicide (pH of 2-4) resulted in a log reduction of only approximately 1.0. Thus, solutions of the present invention are generally effective at pH values from 4.0 to 10 and desirably from about pH 6 to about pH 8.

It is known that the ethyl lactate component of the decontamination aqueous solution deactivates chlorine. Since dichloroisocyanuric acid is a chlorine-based oxidative compound, it was thought that the use of ethyl lactate would impede and prohibit antimicrobial activity. Various amounts of ethyl lactate were added to a 10% bleach solution and the results thereof are shown in FIG. 6.

Figure 6:
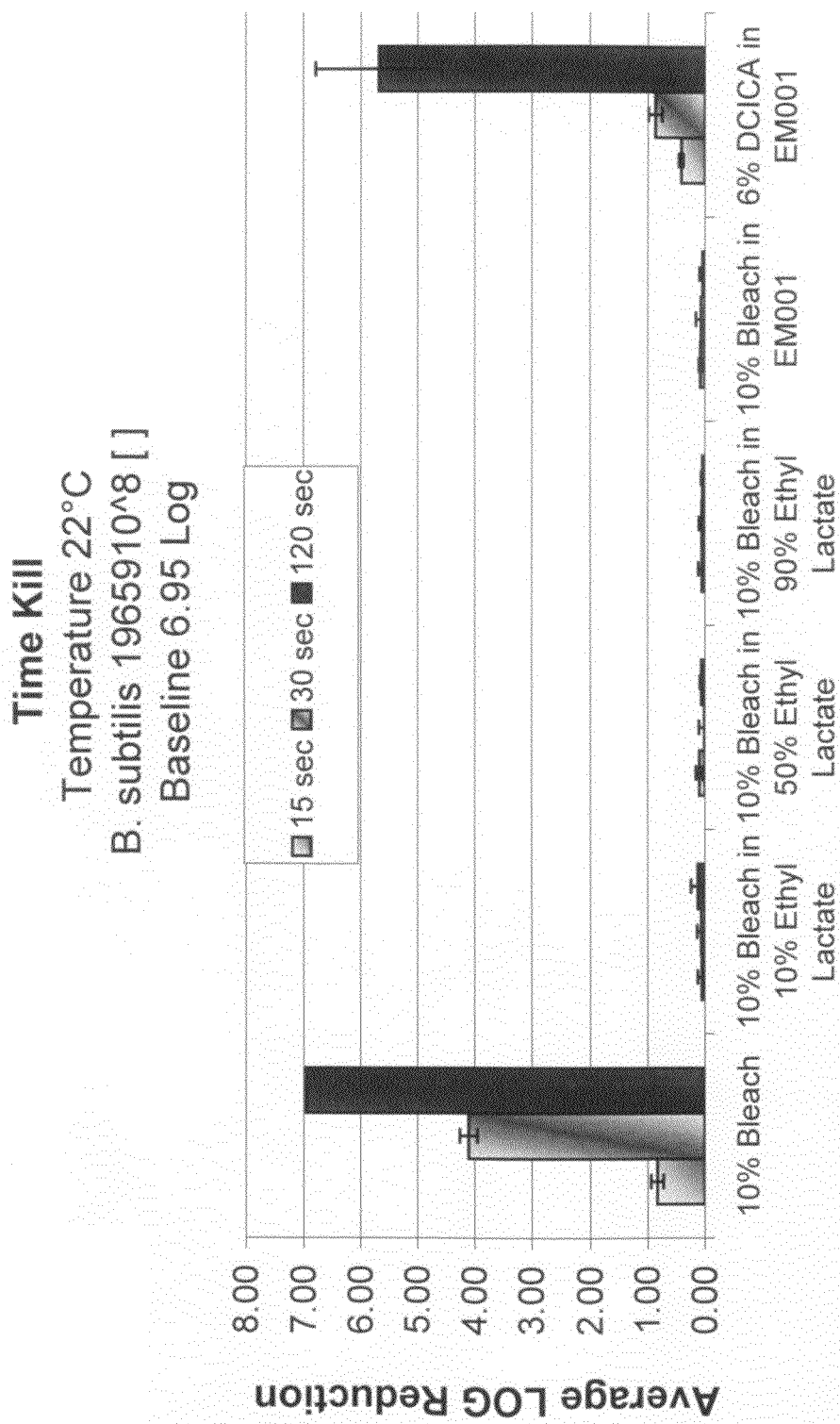
FIG. 6 relates to the adverse effect ethyl lactate has upon bleaching solutions.

As apparent from FIG. 6, a 10% bleach solution was effective in achieving a log 7.0 reduction with regard to *B. Subtilis*. However, when various amounts of ethyl lactate was added thereto; the bleach solution was essentially rendered completely inoperative. Even when bleach was added to the present invention, i.e. Formula EM 1001, it was rendered innocuous. However, when applicants' decontamination aqueous solution containing the noted amounts of components set forth in FIG. 6 was utilized (no bleach), a log reduction of approximately 6 was unexpectedly achieved. In other words, ethyl lactate had no effect whatsoever on the chlorine content of dichloroisocyanuric acid. Thus, proof of unexpected results has been presented.

In order to achieve the above noted good properties of the present invention including low freezing points, low vapor pressure, non-flammability, low viscosity, compound compatibility, and environmental friendliness, various compounds that are detrimental to such properties are avoided including various imadazole compounds; various metal carbonate compounds; various organosilicon compounds, that is compounds containing a silicon atom such as silanes, cyclic or linear siloxanes, various silicates, and the like; various bleaches; various high molecular weight glycols such as those having 6 carbon atoms and higher; and various glycol ethers and various glycol polymers such as polyethylene glycol and polypropylene glycol; Thus, the amounts of such compounds utilized with regard to each package of the one package system or the two package system is low, that is generally about less than 10 parts by weight, desirably less than about 5 parts by weight, and preferably less than about 2 parts by weight, and most preferably nil, that is no compounds thereof, per 100 parts by weight of the one or more polar solvents and quasi-hydrophilic compounds. That is, the aqueous decontamination compositions are essentially free of such compounds.

Figure 7:
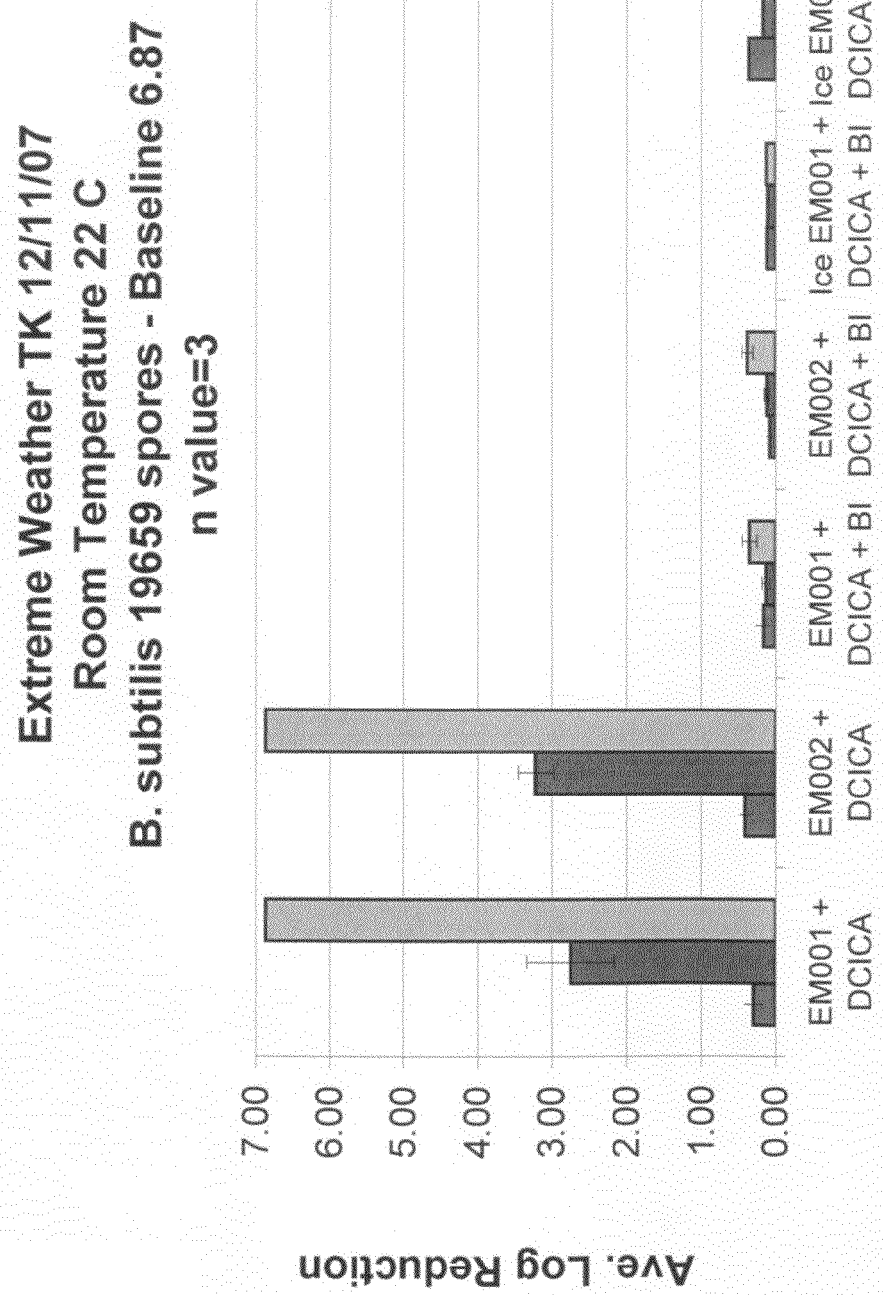
FIG. 7 relates to the adverse effect benzimidazole has upon DCICA solutions.

For example, when an imidazole compound, e.g. benzimidazole (90 mM), was added to the decontamination solution EM1001 or EM1002 of the present invention, it substantially inhibited any log kill of *B. subtilis*, see FIG. 7. Thus, various imidazole compounds are excluded from the present invention since they deplete sporicidal activity. That is, the various decontaminant aqueous solutions of the present invention are free of any imidazole compound or contain only a very small amount thereof as noted above.

Metal carbonates such as sodium carbonate are excluded from the invention since they have been found to reduce the amount of *B. subtilis* kill utilizing EM1001. Thus, if any sodium carbonate is utilized, very small amounts thereof are used as noted above.

As noted, the various excluded silicon containing compounds include silicates or salts thereof, silanes, as well as linear and cyclo polysiloxanes because they often add slippage to the composition and thus reduce adherence to the applied substrate as well as render the aqueous decontaminant composition less environmentally friendly.

It is also within the scope of the present invention to exclude bleaches such as various hydrogen peroxide bleaches, various perborate bleaches such as sodium perborate, various pyrophosphate bleaches such as sodium pyrophosphate; sodium percarbonate; sodium peroxide; various persulfate bleaches, various hypochlorite bleaches, and the like. That is the solutions of the present invention are essentially free thereof and if utilized they contain a very small amount as noted above.

Other compounds that are excluded from the present invention include high alkyl glycols, i.e. $C_6$ and higher, and glycol ethers, i.e. ethers containing 6 or more carbon atoms or repeat groups thereof as well as polymeric glycols such as polyethylene glycol and polypropylene glycol. Thus, the aqueous decontamination compositions of the present invention are essentially free of such glycols and glycol ethers and if utilized, they contain very small amounts thereof as noted above.

As set forth above, an important aspect of the present invention is to utilize high amounts of polar solvents, for example water and various alkyl glycols. That is, the total amount of the polar solvents of the present invention are generally at least about 30% or at least about 35% by weight, desirably at least about 40% by weight, and preferably at least about 60% by weight of polar solvent based upon the total weight of all polar solvents and all quasi hydrophilic compounds.

While in accordance with the patent statutes, the best mode and preferred embodiment have been set forth, the scope of the invention is not limited thereto, but rather by the scope of the attached claims.

What is claimed is:

1. An extreme temperature aqueous decontamination solution, comprising:
    a metal salt of dichloroisocyanuric acid or of a dibromoisocyanuric acid;
    an aqueous solvent system comprising water and at least one alkyl glycol having from 2 to about 4 carbon atoms; the amount of said alkyl glycol being from about 20% to about 80% by weight based upon the total weight of said water and said alkyl glycol;
    and least one hydrophilic compound comprising an alkyl lactate having from 1 to about 10 carbon atoms;
    wherein the amount of said aqueous solvent system is from about 35% to about 90% by weight based upon the total weight of said aqueous solvent system and said hydrophilic compounds;
    wherein the amount of said metal salt of dichloroisocyanuric acid or said dibromoisocyanuric acid is from about 1 part to about 10 parts by weight per 100 parts by weight of said aqueous solvent system and said hydrophilic compounds;
    wherein said extreme temperature decontamination composition is essentially free of any organosilicon containing compounds, and
    wherein said extreme temperature decontamination composition is essentially free of any bleach.

2. The extreme temperature aqueous decontamination solution of claim 1, wherein said metal salt is an alkali metal;
    wherein said alkyl lactate has from 1 to about 3 carbon atoms;
    wherein the amount of any said organosilicon containing compound is about 5 parts by weight or less per 100 parts by weight of said aqueous solvent system and said hydrophilic compounds; and
    wherein the amount of any said bleach is about 5 parts by weight or less per 100 parts by weight of said aqueous solvent system and said hydrophilic compounds.

3. The extreme temperature aqueous decontamination solution of claim 2, wherein said alkyl glycol is ethylene glycol or propylene glycol, wherein the amount of said aqueous solvent system is from about 40% to about 80% by weight based upon the total weight of said aqueous solvent system and said hydrophilic compounds, wherein the amount of said salt of said dichloroisocyanuric acid or said dibromoisocyanuric acid is from about 2 parts to about 9 parts by weight per 100 total parts by weight of said aqueous solvent system and said hydrophilic compounds, and wherein the pH of said decontamination solution is from about 4 to about 8.

4. The extreme temperature aqueous decontamination solution of claim 3, wherein said alkali metal salt is sodium or potassium, wherein said alkyl glycol is propylene glycol, wherein said alkyl lactate is ethylene lactate, wherein the amount of said alkyl glycol is from about 30% to about 70% by weight based upon the total amount of said water and said alkyl glycol;
    wherein the amount of any said organosilicon containing compound is from about 2 parts by weight or less per 100 parts by weight of said aqueous solvent system and said hydrophilic compounds; and
    wherein any amount of said bleach is about 2 parts by weight or less per 100 parts by weight of said aqueous solvent system and said hydrophilic compounds.

5. The extreme temperature aqueous decontamination solution of claim 4, wherein the amount of said aqueous solvent system is from about 55% to about 70% by weight based upon the total weight of said aqueous solvent system and said hydrophilic compounds; and
    wherein the amount of dichloroisocyanuric acid or said dibromoisocyanuric acid is from about 3.5 parts to about 8 parts by weight per 100 parts by weight of said aqueous solvent system and said hydrophilic compounds.

6. The extreme temperature aqueous decontamination solution of claim 1, further comprising an alkyl carbonate having from 2 to about 4 carbon atoms in an amount of from about 2 parts to about 20 parts by weight per 100 parts by weight of said aqueous solvent system and said hydrophilic compounds.

7. The extreme temperature aqueous decontamination solution of claim 4, further comprising an alkyl carbonate having from 2 to about 4 carbon atoms in an amount of from about 4 parts to about 17 parts by weight per 100 parts by weight of said aqueous solvent system and said hydrophilic compounds.

8. The extreme temperature aqueous decontamination solution of claim 1, wherein said aqueous decontamination solution is capable of achieving a microorganism or a bioterrorism agent log reduction of at least about 5.

9. The extreme temperature aqueous decontamination solution according to claim 4, wherein said aqueous decontamination solution is capable of achieving a microorganism or a bioterrorism agent log reduction of at least about 6.

10. A plurality of packages for forming an extreme temperature aqueous decontamination solution, comprising;
a first package comprising a metal salt of dichloroisocyanuric acid or of a dibromoisocyanuric acid; and
a second package comprising a solvent system comprising water and at least one alkyl glycol having from about 2 about 4 carbons; the amount of said alkyl glycol being from about 20% to about 80% by weight based upon the total weight of said water and said alkyl glycol; and at least one hydrophilic compound comprising an alkyl lactate having from about 1 to about 10 carbon atoms; wherein the amount of said aqueous solvent system is from about 35% to about 90% by weight based upon the total weight of said aqueous solvent system and said hydrophilic compounds;
wherein the amount of said metal salt of dichloroisocyanuric acid or said dibromoisocyanuric acid in said first package is from about 1 part to about 10 parts by weight per 100 parts by weight of said aqueous solvent system and said hydrophilic compounds;
wherein said first package and said second package are essentially free of any organosilicon containing compounds, and
wherein said first package and said second package are essentially free of any bleach.

11. The extreme temperature aqueous decontamination solution of claim 10, wherein said metal salt is an alkali metal; wherein said alkyl lactate has from 1 to about 3 carbon atoms;
wherein the amount of any said organosilicon containing compound is about 5 parts by weight or less per 100 parts by weight of said aqueous solvent system and said hydrophilic compounds: and
wherein the amount of any said bleach is about 5 parts by weight or less per 100 parts by weight of said aqueous solvent system and said hydrophilic compounds.

12. The extreme temperature aqueous decontamination solution of claim 11, wherein said alkyl glycol is ethylene glycol or propylene glycol, and wherein the amount of said aqueous solvent system is from about 40% to about 80% by weight based upon the total weight of said aqueous solvent system and said hydrophilic compounds.

13. The extreme temperature aqueous decontamination solution of claim 12, wherein said alkali metal salt is sodium or potassium, wherein said alkyl glycol is propylene glycol, wherein said alkyl lactate is ethylene lactate, wherein the amount of said alkyl glycol is from about 30% to about 70% by weight based upon the total amount of said water and said alkyl glycol; wherein the amount of said aqueous solvent system is from about 55% to about 70% by weight based upon the total weight of said aqueous solvent system and said hydrophilic compounds;
wherein the amount of said dichloroisocyanuric acid or said dibromoisocyanuric acid is from about 3.5 parts to about 8 parts by weight based upon the total weight of said aqueous solvent system and said hydrophilic compounds;
wherein the amount of any said organosilicon containing compound is about 2 parts or less by weight per 100 parts by weigh to said aqueous solvent system and said hydrophilic compounds; and
wherein any amount of any said bleach is about 2 parts by weight or less per 100 parts by weight of said aqueous solvent system and said hydrophilic compounds.

14. The extreme temperature aqueous decontamination solution of claim 10, that further comprises an alkyl carbonate having from 2 to about 4 carbon atoms in an amount of from about 2 parts to about 20 parts by weight per 100 parts by weight or said aqueous solvent system and said hydrophilic compounds.

15. The extreme temperature aqueous decontamination solution of claim 10, wherein said aqueous decontamination solution is capable of achieving a microorganism or a bioterrorism agent log reduction of at least about 5.

16. A process for forming an extreme temperature aqueous decontamination solution, comprising the steps of:
providing a metal salt of dichloroisocyanuric acid or of a dibromoisocyanuric acid;
providing an aqueous solvent system comprising including water and at least one alkyl glycol having from 2 to 4 carbon atoms; the amount of said alkyl glycol being from about 20% to about 80% by weight based upon the total weight of said water and said alkyl glycol;
providing at least one hydrophilic compound comprising an alkyl lactate having from 1 to about 10 carbon atoms; wherein the amount of said aqueous solvent system is from about 35% to about 90% by weight based upon the total weight of said aqueous solvent system and said hydrophilic compounds; wherein the total amount of said metal salts of dichloroisocyanuric acid or of a dibromoisocyanuric acid is from about 1 part to about 10 parts by weight per 100 parts by weight of said aqueous solvent system and said hydrophilic compounds; and
mixing said metal salt of dichloroisocyanuric acid or of dibromoisocyanuric acid, said aqueous solvent system; and said hydrophilic compounds and forming an aqueous decontamination solution.

17. The process of claim 16, wherein said metal salt is an alkali metal;
wherein said alkyl lactate has from 1 to about 3 carbon atoms.

18. The process of claim 17, wherein said alkali metal salt is sodium or potassium, wherein said alkyl glycol is ethylene glycol or propylene glycol, wherein said alkyl lactate is ethylene lactate, wherein the amount of said alkyl glycol is from about 30 to about 70% by weight based upon the total amount or said water and said alkyl glycol;
wherein the amount of said aqueous solvent system is from about 40% to about 80% by weight based upon the total weight of said aqueous solvent system and said hydrophilic compounds,
wherein the amount of said metal salt of said dichloroisocyanuric acid or said dibromoisocyanuric acid is from about 2 parts to about 9 parts by weight per 100 total parts by weight of said aqueous solvent system and said-hydrophilic compounds;
wherein said aqueous decontamination solution contains about 5 parts by weight or less of an organosilicon containing compound per 100 parts by weight of said aqueous solvent system and said hydrophilic compounds; and
wherein said aqueous decontamination solution contains about 5 parts by weight or less of a bleach per 100 parts by weight of said aqueous solvent system and said hydrophilic compounds.

19. The process of claim 18, wherein the amount of said aqueous solvent system is from about 55% to about 70% by weight based upon the total weight of said aqueous solvent system and said hydrophilic compounds; and
wherein the amount of said metal salt of dichloroisocyanuric acid or of dibromoisocyanuric acid is from about 3.5 parts to about 8 parts by weight per 100 parts by weight of said aqueous solvent system and said hydrophilic compounds.

* * * * *

UNITED STATES PATENT AND TRADEMARK OFFICE
CERTIFICATE OF CORRECTION

PATENT NO.        : 8,518,941 B2
APPLICATION NO.   : 12/806731
DATED             : August 27, 2013
INVENTOR(S)       : Herbert J. Kaiser et al.

Page 1 of 1

It is certified that error appears in the above-identified patent and that said Letters Patent is hereby corrected as shown below:

In the Claims:

In claim 16, column 14, line 19, the word "including" should be omitted.

Signed and Sealed this
Twelfth Day of November, 2013

Teresa Stanek Rea
*Deputy Director of the United States Patent and Trademark Office*